United States Patent
Cazaux et al.

(10) Patent No.: US 9,663,461 B2
(45) Date of Patent: May 30, 2017

(54) METHOD FOR SYNTHESISING A MERCAPTAN BY ADDING HYDROGEN SULFIDE TO AN OLEFIN

(71) Applicant: Arkema France, Colombes (FR)

(72) Inventors: Jean-Benoit Cazaux, Billere (FR); Delphine Ostorero, Sauvagnon (FR)

(73) Assignee: Arkema France, Colombes (FR)

(*) Notice: Subject to any disclaimer, the term of this patent is extended or adjusted under 35 U.S.C. 154(b) by 0 days.

(21) Appl. No.: 15/031,060

(22) PCT Filed: Oct. 22, 2014

(86) PCT No.: PCT/FR2014/052692
§ 371 (c)(1),
(2) Date: Apr. 21, 2016

(87) PCT Pub. No.: WO2015/059412
PCT Pub. Date: Apr. 30, 2015

(65) Prior Publication Data
US 2016/0257646 A1 Sep. 8, 2016

(30) Foreign Application Priority Data
Oct. 24, 2013 (FR) ...................... 13 60377

(51) Int. Cl.
*C07C 319/04* (2006.01)
*C07C 319/16* (2006.01)
(Continued)

(52) U.S. Cl.
CPC ............ *C07C 319/04* (2013.01); *B01J 21/04* (2013.01); *B01J 23/26* (2013.01); *C07C 319/16* (2013.01); *Y02P 20/582* (2015.11)

(58) Field of Classification Search
None
See application file for complete search history.

(56) References Cited

U.S. PATENT DOCUMENTS 2,434,510 A  1/1948  Olin
2,443,852 A  6/1948  Eaton
(Continued)

FOREIGN PATENT DOCUMENTS

EP  0354460  2/1990
FR  2844794  3/2004
(Continued)

OTHER PUBLICATIONS

International Search Report and Written Opinion for International Application No. PCT/FR2014/052692, dated Feb. 19, 2015, 8 pages.

*Primary Examiner* — Rosalynd Keys
(74) *Attorney, Agent, or Firm* — RatnerPrestia (57) ABSTRACT

The invention relates to a method for synthesising a mercaptan from a terminal olefin and hydrogen sulphide which comprises the following consecutive steps: A—catalytic addition of hydrogen sulphide to a terminal olefin catalysed by an acid catalyst; B—separation of the products of the addition reaction into a light fraction including the surplus hydrogen sulphide and the olefins, and into a heavy fraction including at least one mercaptan and optionally one or more thioethers; C—a finishing step of passing the light fraction obtained in step B over an acid catalyst; then D—separation of the products of the finishing step into a fraction that is rich in hydrogen sulphide and into a fraction that is rich in additives; and finally E—recirculation of the fraction that is rich in hydrogen sulphide to the catalytic addition step A. The invention also relates to the facility for implementing said method.

16 Claims, 2 Drawing Sheets

(51) Int. Cl.
*B01J 21/04* (2006.01)
*B01J 23/26* (2006.01)

(56) References Cited

U.S. PATENT DOCUMENTS

| | | |
|---|---|---|
| 2,531,601 A | 11/1950 | Bell |
| 2,950,324 A | 8/1960 | Loev |
| 2,951,875 A | 9/1960 | Loev |
| 3,036,133 A | 5/1962 | Goshorn |
| 4,059,636 A | 11/1977 | Kubicek |
| 4,102,931 A | 7/1978 | Buchholz |
| 4,565,893 A | 1/1986 | Arretz |
| 4,927,972 A | 5/1990 | Arretz |
| 5,113,034 A | 5/1992 | Soled |
| 6,133,496 A | 10/2000 | Lin |
| 6,162,952 A | 12/2000 | Cook |
| 2006/0025633 A1 | 2/2006 | Fremy |
| 2006/0111591 A1 | 5/2006 | Fremy |
| 2006/0247475 A1 | 11/2006 | Hasenberg |

FOREIGN PATENT DOCUMENTS

| | | |
|---|---|---|
| GB | 602238 | 5/1948 |
| JP | 6277342 | 4/1987 |

METHOD FOR SYNTHESISING A MERCAPTAN BY ADDING HYDROGEN SULFIDE TO AN OLEFIN

CROSS-REFERENCE TO RELATED APPLICATIONS

This is the national phase of International Application No. PCT/FR2014/052692, filed 22 Oct. 2014, which claims priority to French Application No. 1360377, filed 24 Oct. 2013. The disclosure of each of these applications is incorporated herein by reference in its entirety for all purposes.

FIELD OF THE INVENTION

The present invention relates to the field of mercaptans (also called thiols) and relates more particularly to a process for synthesis of a mercaptan by catalytic addition of hydrogen sulphide to a terminal olefin.

The invention also relates to an installation for carrying out this process.

DISCUSSION OF THE RELATED ART

Many studies have been undertaken with a view to developing the preparation of these compounds, owing to the industrial interest in the mercaptans or thiols (cf. Forquy, Arretz, *Heterogeneous Catalysis in Mercaptan Industrial Synthesis, Studies in Surface Science and Catalysis*, Volume 41, (1988), pages 91-104).

For example, a widely used process is known that employs the reaction of thiolation of alcohols by hydrogen sulphide in the presence of a catalyst of the alumina type impregnated with metal oxides, for example oxides of tungsten or of caesium as well as alkaline derivatives. This thiolation is used for example in the case of synthesis of primary mercaptans.

The process employing addition of hydrogen sulphide to an olefin is also known. Addition of hydrogen sulphide to an olefin is a reaction of sulphydration which may be oriented according to the Markovnikov or conversely the anti-Markovnikov rule, depending on whether we are in catalytic or radical conditions (photochemistry for example). Sulphydration processes have been proposed, with the aim of reacting hydrogen sulphide ($H_2S$) with an olefin under pressure in the presence of various catalysts. This synthesis is described very well in the literature (Reid, *Organic chemistry of bivalent sulfur*, Vol. I, 20, (1958)) and employs various types of catalysts, such as homogeneous acid catalysts ($AlCl_3$ as described in document U.S. Pat. No. 2,531,601, or $BF_3$ as described in documents GB 602,238, U.S. Pat. No. 2,434,10 and U.S. Pat. No. 2,443,852) or heterogeneous catalysts with strong acid sites (cation exchange resins as described in document U.S. Pat. No. 4,565,893, exchanged zeolites as described in document U.S. Pat. No. 4,102,931) or supported phosphoric acid (U.S. Pat. No. 2,950,324), silica with small amounts of alumina (U.S. Pat. No. 2,951,875), aluminas whether or not impregnated with metal oxides (U.S. Pat. No. 6,162,952) or heteropolyacids (U.S. Pat. No. 3,036,133, FR 2 844 794).

The applicant aims in particular to improve the yield of this reaction of catalytic addition of hydrogen sulphide to a terminal olefin. In fact, this addition reaction leads to a certain number of by-products, derived notably from the anti-Markovnikov reactions, reactions of isomerization of the double bond as well as the reaction of addition of the mercaptan (formed in the main reaction) to the starting reactant, i.e. the olefin, leading to the formation of thioethers.

Some of these impurities, such as the internal olefins, may generate significant constraints, such as accumulation of unreactive compounds, on the process and cannot be purged, for obvious economic reasons.

The performance of the viability of such a process is compromised considerably by the presence of such impurities.

The thioethers obtained as by-products in the preparation of mercaptans generally are of no commercial interest and represent a loss of yield, which it is always useful to limit as far as possible to optimize both the production efficiency and the cost of the purification steps.

Consequently, the applicant aims to improve this process.

SUMMARY OF THE INVENTION

Research has been conducted on the catalyst, in order to improve its selectivity, notably so as to increase the yield of thiol. However, the applicant did not choose to work on the catalyst here, but concentrated on improvement of the process as such.

The technical problem was solved by adding a finishing step, which follows the step of addition of hydrogen sulphide to the olefin and a step of recycling the unreacted raw materials.

Consequently, the invention relates to a process for synthesis of a mercaptan from a terminal olefin and hydrogen sulphide comprising at least the following successive steps:

A—catalytic addition of hydrogen sulphide to a terminal olefin, catalysed by an acid catalyst, then B—separation of the products of the addition reaction into
   a light fraction comprising the excess hydrogen sulphide and the olefins, and
   a heavy fraction comprising at least one mercaptan and optionally one or more thioethers, C—finishing step, passing the light fraction obtained from step B over an acid catalyst, then D—separation of the products from the finishing step into
   a fraction rich in hydrogen sulphide and
   a fraction rich in addition products and then E—recycling of the fraction rich in hydrogen sulphide to the step of catalytic addition A.

The invention also relates to an installation for carrying out the process according to the invention.

Other aims, features and advantages of the invention will become clear on reading the following description and the appended FIGS. 1 to 4, which illustrate embodiments of the installation according to the invention, and from the examples given below.

Moreover, any range of values denoted by the expression "between a and b" represents the range of values from more than a to less than b (i.e. limits a and b excluded), whereas any range of values denoted by the expression "from a to b" signifies the range of values from a up to b (i.e. including the limits a and b).

DETAILED DESCRIPTION OF CERTAIN EMBODIMENTS OF THE INVENTION

Addition Step

The process according to the invention begins with a step of catalytic addition of hydrogen sulphide to a terminal olefin.

Hydrogen Sulphide

Hydrogen sulphide is used in the process in a sufficient amount to obtain conversion of the olefin. In general, this amount may correspond to a molar ratio H$_2$S/olefin from 1 to 100, preferably from 2 to 30, more preferably from 2 to 12. Preferably, hydrogen sulphide is used in excess in the addition reaction. This addition of hydrogen sulphide in excess is able to promote the reaction of formation of thiol relative to the competing reactions of formation of thioether or of oligomers.

Preferably, the addition step is carried out under pressure of hydrogen sulphide. Preferably, the pressure is from 1 MPa to 2 MPa. These conditions make it possible to increase the level of conversion at equivalent amount of catalyst by varying the parameter of residence time. The process may be carried out as a continuous process or as a batch process. Preferably, it is a continuous process.

The liquid hourly space velocity, defined as the ratio of the hourly volume flow rate of olefin and of hydrogen sulphide (in the synthesis conditions) to the volume of catalyst may vary considerably depending on the activity of the catalyst. This value is generally between 1 and 150 h$^{-1}$, preferably between 50 and 150 h$^{-1}$.

Terminal Olefin

Terminal olefin means, in the sense of the present invention, an unsaturated hydrocarbon, whose double bond is necessarily located at one end of the hydrocarbon chain.

Preferably, the olefin used as starting reactant may be of the following general formula (1):

$$R_1R_2C=CH_2 \qquad (1),$$

in which $R_1$ denotes a hydrogen atom, and $R_2$ represents an alkyl radical with from 1 to 20 carbon atoms, preferably from 2 to 20 carbon atoms, and more particularly from 2 to 12 carbon atoms, linear, branched or cyclic. The radical $R_2$ is optionally substituted with a group that is inert with respect to the reaction in question. For example, but not restrictively, this group may be selected from: cycloalkyl, aryl, carboxy (—COOH), alkylcarbonyl (—C(O)OR), alkoxy (—OR), alkylcarbonyl-oxycarbonyl (—C(O)—O—C(O)—R), cyano (—CN), thiocarboxy (—C(S)—OH), mercaptocarbonyl (—C(O)—SH), alkoxy(thiocarbonyl) (—C(S)—OR), (alkylthio)carbonyl (—C(O)—SR), alkylcarbonylthiocarbonyl (—C(O)—S—C(O)—R), halogen atom, sulpho (—SO$_3$H), thionyl (R—S(O)—), alkylsulphonyl (R—S(O$_2$)—), alkoxysulphonyl (RO(O$_2$)—), radicals comprising silane functions and/or siloxanes and/or phosphates.

R represents an alkyl radical with from 1 to 20 carbon atoms, preferably from 2 to 20 carbon atoms, and more particularly from 2 to 12 carbon atoms, linear, branched or cyclic.

The olefins preferably used are the C$_3$ to C$_{20}$ terminal linear olefins. The preferred olefins are selected from 1-butene, 1-pentene, 1-hexene, 1-heptene, 1-octene, 1-nonene, 1-decene, 1-undecene and 1-dodecene. More particularly, 1-butene is used. The reaction of sulphydration leads in this case to 2-butanethiol.

Catalyst

The process according to the invention uses an acid catalyst, preferably a solid acid catalyst, which corresponds to a reaction under heterogeneous catalysis.

Preferably, these catalysts are selected from:
one or more heteropolyacid(s) selected from:
(i) a compound of formula: H$_3$PW$_{12}$O$_{40}$,nH$_2$O, H$_4$SiW$_{12}$O$_{40}$,nH$_2$O or H$_6$P$_2$W$_{18}$O$_{62}$,nH$_2$O, in which n is an integer representing the number of molecules of water of crystallization, generally between 0 and 30, preferably between 6 and 20; and
(ii) a potassium, rubidium, caesium or ammonium salt of at least one compound (i) or a mixture of such salts;
a sulphated zirconia,
a tungstenated zirconia,
a zeolite,
a cationic resin, and
metal oxides.

The heteropolyacid (i) is generally obtained by the condensation of two or more different oxo-acids, such as phosphoric acid, silicic acid or tungstic acid. It is soluble in water or in a polar organic solvent. The compound of formula: H$_3$PW$_{12}$O$_{40}$,nH$_2$O is known by the name of 12-phosphotungstic acid or 12-tungstophosphoric acid, and is commercially available. The compound of formula: H$_4$SiW$_{12}$O$_{40}$,nH$_2$O is known by the name of 12-tungstosilicic acid or 12-silicotungstic acid, and is also commercially available.

The compound of formula: H$_6$P$_2$W$_{18}$O$_{62}$,nH$_2$O may be prepared according to the procedure described in the following reference: A. P. Ginsberg, *Inorganic Synthesis*, Vol. 27, published by J. Wiley & Sons (1990) pages 105-107.

The heteropolyacid (ii) is a salt obtained by partial substitution of one or more protons of the heteropolyacid (i) with the corresponding cation. It will be clear to a person skilled in the art that such a substitution cannot be total, otherwise the acidity would be lost. Such a salt is prepared from a solution of the heteropolyacid (i), to which the desired amount of the precursor of the alkali or ammonium is added.

The preferred precursor is the corresponding chloride or carbonate. The precipitated salt is separated, and then dried in mild conditions, preferably by centrifugation followed by lyophilization. We may mention as reference: N. Essayem, G. Coudurier, M. Fournier, J. C. Vedrine, *Catal. Lett.,* 34 (1995) pages 224-225.

These heteropolyacids may be deposited on known supports, such as activated carbon, alumina, zirconia, silica, thorium oxide, pumice stone, and silica-alumina compositions.

Sulphated zirconia is prepared by impregnation of sulphuric acid on a zirconium oxide support by the method described in the reference: F. R. Chen, G. Coudurier, J-F Joly and J. C. Vedrin, J. Catal., 143 (1993) page 617.

Tungstenated zirconia is prepared by impregnation of tungsten oxide on a zirconium oxide support, by the method described in the patent Soled et al. (U.S. Pat. No. 5,113,034).

All the various polymers and copolymers with acid functions known in the art as cation exchangers may also be suitable as catalyst for use according to the invention. In particular, it is possible to use crosslinked resins based on sulphonated polystyrene, in particular with divinylbenzene, acrylic or phenylacrylic resins with free carboxyl groups, resins of the phenol-formaldehyde type derived from phenol-sulphonic acids, ligno-sulphonic exchangers, etc. Resins of this kind are available commercially with various names, in particular Allassion®, Cecacit®, Wofatites®, Levatites®, Imac®, Ionac®, Amberlites®, Amberlyst®, Liquorex®, Zeorex®, Zeocarb®, Dowex®, etc. The sulphonated copolymers of styrene with divinylbenzene are quite particularly suitable, for example those that are available commercially with the names Amberlyst®, Lewatit® or Dowex®; moreover, the copolymers of tetrafluoroethylene with a perfluorosulphonic acid (in particular perfluoro-3,6-dioxa-4-methyl-7-octene sulphonic acid) known by the trade name Nafion® may be used advantageously. Regardless of which resin is used as catalyst, it is necessary to ensure that it does not contain more than 0.5% of water, determinable after 6 hours of drying at 80° C. (advantageously less than 0.2 wt % of water).

It is also possible to use oxides of molybdenum, oxides of cobalt, oxides of chromium or cobalt molybdate on alumina. These may be deposited on known supports, such as activated carbon, alumina, zirconia, silica, thorium oxide, pumice stone, and silica-alumina compositions.

Preferably, in the addition step, a catalyst of the Lewis acid type is used. Preferably, a catalyst of the Brønsted acid type is used for the finishing step.

Preferably, the catalyst used in the addition step is a catalyst comprising Lewis acid sites.

Preferably, the heterogeneous catalyst comprising Lewis acid sites is selected from the oxides of molybdenum, oxides of cobalt, oxides of chromium, cobalt molybdate, and phosphotungstic acids deposited on supports selected from activated carbon, alumina, zirconia, silica, thorium oxide, pumice stone and silica-alumina compositions, and more particularly chromium oxide supported on alumina.

Preferably, the catalyst used for the finishing step is different from the catalyst used in the first addition reaction in order to maximize the conversion.

In the first part of the reaction, the reactants described above are brought into contact, in the presence of a charge of the catalytic composition defined above.

This process may be carried out in the gas phase or liquid phase or gas/liquid phase. In a preferred embodiment, the reaction is carried out in the gas phase, provided that the conditions of temperature and pressure used are such that the reactants and the products are in the gaseous state.

The process is preferably carried out in a reactor fed with the reactants continuously, but a reactor of the batch type may also be used.

The reaction temperature varies depending on the olefin used and the desired degree of conversion, but is generally within a range from 30 to 350° C., preferably from 100 to 350° C.

Separation Step

There then follows a step of separation of the products of the addition reaction into a light fraction comprising the excess hydrogen sulphide and the terminal and/or internal olefins, and a heavy fraction comprising at least one mercaptan and optionally one or more thioethers.

The fraction intended for the finishing step is the light fraction. It comprises the unreacted reactants: hydrogen sulphide added in excess in the reactor, terminal olefin and olefin isomerized under the effect of the acidic reaction environment.

In fact, under the effect of the acidic environment, migration of the terminal double bond was observed. The olefins obtained are called "internal olefin" on account of this migration of the double bond located at one end of the chain to the interior of the chain.

The second fraction to be kept comprises the products of the addition reaction: the predominant products of the addition according to Markovnikov, the products of the anti-Markovnikov addition and sulphides or thioethers.

Owing to the molecular weights of these species in the reaction mixture, distillation may be an appropriate method of separation. Gas/liquid separation is also possible.

Finishing Step

The light fraction obtained from separation step B, i.e. the reactants not converted to mercaptan or sulphides in the addition reactor, are treated in a catalytic finishing reactor of appropriate technology (fixed bed, multiple-tube, fluidized bed, etc.), optionally in the presence of an additional amount of hydrogen sulphide fed directly into the finishing reactor.

The process according to the invention uses an acid catalyst, preferably a solid acid catalyst, which corresponds to a reaction under heterogeneous catalysis.

This finishing reactor employs an acid catalyst. This catalyst is an acid catalyst that has strong acid sites. More particularly, it is selected from the cation exchange resins and the zeolites, whether exchanged or not, and notably the supported heteropolyacid, macrocrosslinked sulphonic resin of type Amberlyst® A15, A16, A35, A36, A70. The resins Amberlyst® 35 and 36 dry are particularly preferred. These resins are supplied by the company DOW.

In the finishing step, the catalyst is preferably a macrocrosslinked sulphonic resin, for example that marketed under the name "Amberlyst® 36 dry".

This step may be carried out at a temperature in the range from 100 to 150° C., in the same range of pressure of hydrogen sulphide as the first reaction step. This step makes it possible to convert the isomerized olefins by reacting them on the catalyst with the hydrogen sulphide present in the reactor.

This step may be done in the gas phase or in the liquid phase, continuously or as a batch process. Preferably, it is carried out continuously.

The liquid hourly space velocity, defined as the ratio of the hourly volume flow rate of olefin and of hydrogen sulphide (in the synthesis conditions) to the volume of catalyst, may vary considerably depending on the activity of the catalyst. This value is generally from 1 to 150 $h^{-1}$, preferably from 50 to 150 $h^{-1}$.

Separation Step

There then follows a step of separation of the products from the finishing step into a fraction rich in hydrogen sulphide and a fraction rich in addition products.

The fraction rich in addition products comprises the predominant products of the addition according to Markovnikov, the products of the anti-Markovnikov addition and sulphides.

Recycling

The reactants that did not react during the finishing step: hydrogen sulphide added in excess in the addition reactor and optionally in the finishing reactor and the traces of olefins that had still not reacted even in the finishing step, are recycled to the addition reactor to undergo the addition reaction once again.

The recycling step may comprise a purge, for preventing accumulation of by-products that do not react.

Preferably, the process described above leads to the synthesis of secondary mercaptans.

According to a first embodiment, the process according to the invention may comprise an additional purification step F at the end of the process.

The heavy fraction obtained from separation step B and the fraction rich in addition products obtained from separation step E, each comprising at least one mercaptan and optionally one or more sulphides, are combined and purified in order to isolate the expected mercaptan or mercaptans.

Owing to the molecular weights of the species present in the reaction mixture, distillation may be an appropriate method of separation. Thus, this step F makes it possible to isolate the secondary mercaptan from the linear mercaptan and the sulphides.

According to a second embodiment, the sulphides resulting from the last purification step F described above are recycled to the finishing step C.

The presence of these sulphides makes it possible to dissipate the heat of reaction of the finishing step. It also allows a sulphydrolysis reaction, which corresponds to reaction of hydrogen sulphide on an alkyl sulphide (preferably branched), allowing release of two molecules of mercaptan.

In fact, it is known from documents U.S. Pat. No. 4,927,972, U.S. Pat. No. 4,059,636 and US 2006/0025633 that sulphides or thioethers can be converted to mercaptan in the presence of hydrogen sulphide and catalysts, such as sulphonic resins, aluminosilicates, 12-phosphotungstic acids supported on alumina or cobalt-molybdenum compositions on alumina, or heteropolyacids on alumina.

Thus, in addition to the reaction of addition of hydrogen sulphide to the internal and terminal olefins present in the reaction mixture, the sulphydrolysis reaction is possible within this reaction mixture.

Consequently, this finishing step makes it possible to improve the yield from the reaction by partly transforming the reaction by-products to marketable mercaptan.

Thus, this second embodiment comprises the following successive steps:
A—catalytic addition of hydrogen sulphide to a terminal olefin catalysed by an acid catalyst, then
B—separation of the products of the addition reaction into
  a light fraction comprising the excess hydrogen sulphide and the olefins, and
  a heavy fraction comprising at least one mercaptan and optionally one or more thioethers
C—finishing step, passing the light fraction obtained from step B over an acid catalyst, then
D—separation of the products from the finishing step into
  a fraction rich in hydrogen sulphide and
  a fraction rich in addition products and then
E—recycling of the fraction rich in hydrogen sulphide to the step of catalytic addition A,
F—purification of the heavy fraction obtained from separation step B and the fraction rich in addition products obtained from separation step E, combined, into
one or more light fractions comprising one or more mercaptans and
  a heavy fraction comprising the sulphides and then
G—recycling the heavy fraction from the preceding purification step F to the finishing step C.

According to a third embodiment, the fractions comprising the mercaptan or mercaptans and the sulphides obtained from separation step B and separation step E are not combined. According to this embodiment, a purification step is provided for each fraction.

Thus, this third embodiment comprises the following steps:
A—catalytic addition of hydrogen sulphide to a terminal olefin catalysed by an acid catalyst, then
B—separation of the products of the addition reaction into
  a light fraction comprising the excess hydrogen sulphide and the olefins, and
  a heavy fraction comprising at least one mercaptan and optionally one or more thioethers,
C—finishing step, passing the light fraction obtained from step B over an acid catalyst, then
D—separation of the products from the finishing step into
  a fraction rich in hydrogen sulphide and
  a fraction rich in addition products then
E—recycling of the fraction rich in hydrogen sulphide to the step of catalytic addition A.
P1—purification of the heavy fraction obtained from separation step B into
one or more light fractions comprising one or more mercaptans and
  a heavy fraction comprising the sulphides and then
G1—recycling of the heavy fraction from the preceding purification step P1 to the finishing step C,
P2—purification of the fraction rich in addition products from separation step D, into
one or more light fractions comprising one or more mercaptans and
  a heavy fraction comprising the sulphides.

Synthesis of 2-butanethiol from 1-butene

The synthesis of 2-butanethiol from 1-butene is now described as a preferred embodiment of the process according to the invention.

Thus, 1-butene leads predominantly to 2-butanethiol, also called sec-butylmercaptan (SBM), according to a Markovnikov addition. The designation secondary mercaptan arises from the fact that the carbon atom bearing the thiol function is a secondary carbon.

The by-products that may be obtained are:
n-butylmercaptan (NBM), which is the product of oriented addition according to an anti-Markovnikov addition,
2-cis-butene and 2-trans-butene, which are the products of isomerization of 1-butene in an acid environment,
sulphides or thioethers, which are the reaction products between butene and the mercaptan.

Varying amounts of the by-products will be obtained, depending on the procedure and the reaction conditions.

The reaction scheme given below illustrates the aforementioned species:

The finishing step included in the process according to the invention has the purpose of converting the butenes-2 by reaction with hydrogen sulphide.

The step of recycling of the sulphides to the finishing step in the liquid phase has the purpose of producing a reaction of sulphydrolysis of the sulphides leading to the production of mercaptans.

Thus, this process allows maximum conversion of the secondary species into marketable mercaptans, thus leading to an increase in yield.

The invention also relates to an installation employing the process described above. The details of the installation according to the invention will become clear on reading the following description, given purely as a non-limiting example, and referring to the appended FIGS. 1 to 4, which illustrate the embodiments of the installation according to the invention.

Installation

Figure 1:
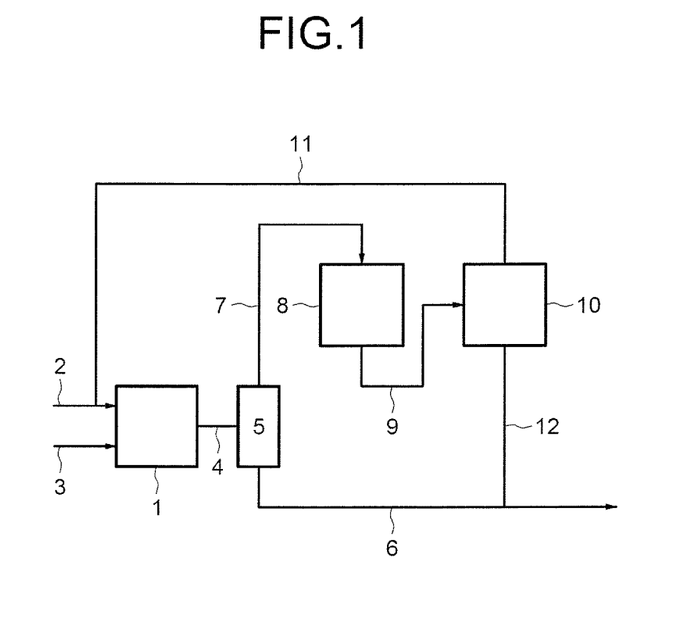

FIG. 1

FIG. 1 describes an installation for synthesis of a mercaptan. The installation comprises an addition reactor (1) for the catalysed addition of hydrogen sulphide to a terminal olefin, supplied with hydrogen sulphide via a pipeline (2), and with terminal olefin via a pipeline (3). Pipeline (4), located at the outlet of the addition reactor (1), supplies a first separating device (5) with a stream of crude reaction mixture.

Pipeline (6), connected to the outlet of the first separating device (5), makes it possible to discharge the heavy fraction comprising the mercaptan or mercaptans and optionally one or more thioethers.

Pipeline (7), also connected to the outlet of the first separating device (5), recovers the light fraction comprising the excess hydrogen sulphide and the olefins. This pipeline (7) supplies a finishing reactor (8).

Pipeline (9) conveys all of the reaction mixture from the finishing reactor (8) to a second separating device (10).

A pipeline (11) located at the outlet of the second separating device (10) recycles the fraction rich in hydrogen sulphide to the addition reactor (1) or to pipeline (2) supplying the addition reactor (1) with raw materials. This pipeline (11) thus allows recycling of the unreacted reactants, notably hydrogen sulphide. This pipeline (11) may comprise a valve for performing a purge of by-products accumulating in the circuit.

Line (12) from the second separating device (10) recovers the fraction rich in addition products to line (6) in order to combine the products resulting from the addition reaction.

Figure 2:
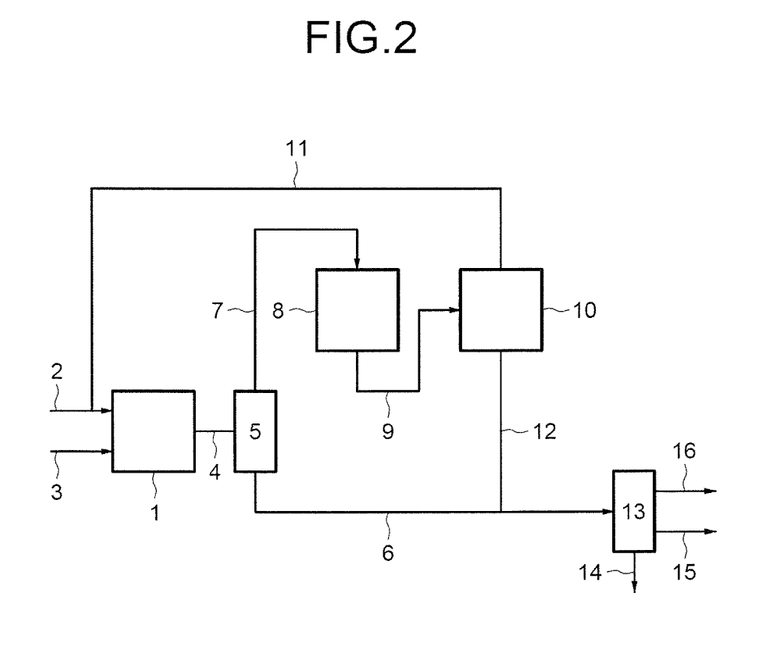

FIG. 2

FIG. 2 is a variant of FIG. 1. The references of FIG. 2 are identical to those of FIG. 1. FIG. 2 comprises an additional purification device (13).

Line (6) conveying the heavy fraction comprising the mercaptan or mercaptans and optionally one or more thioethers and connected to the outlet of the first separating device (5), connected to line (12) from the second separating device (10) and recovering the fraction rich in addition products, supplies the purification device (13). This purification device (13) makes it possible to isolate a secondary mercaptan in a first line (16), a linear mercaptan in a second line (15) and to discharge a heavy fraction comprising the sulphides and other by-products in a third line (14).

Figure 3:
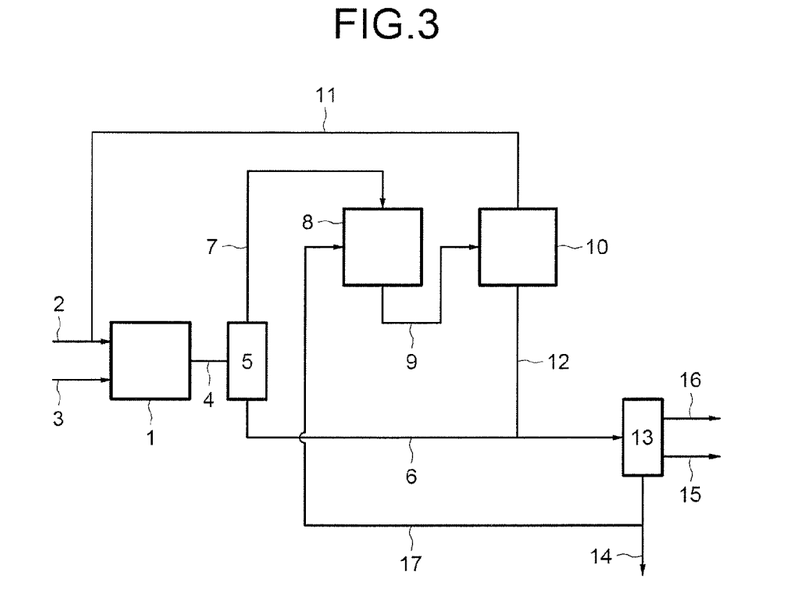

FIG. 3

FIG. 3 is a variant of FIG. 2. The references of FIG. 3 are identical to those of FIG. 2. FIG. 3 comprises an additional line (17).

Line (17) conveying the sulphides and other by-products is connected to the outlet of the purification device (13) and supplies the finishing reactor (8).

Figure 4:
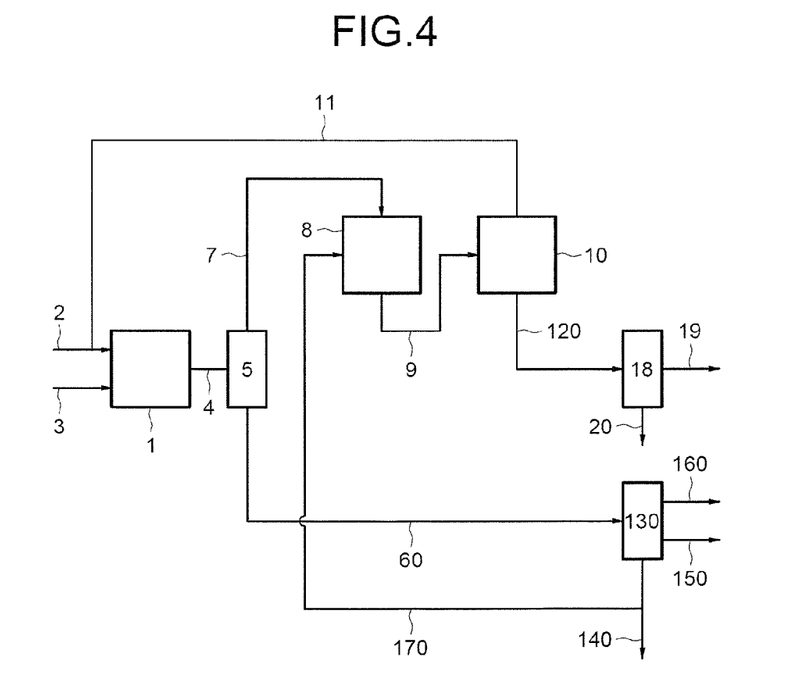

FIG. 4

FIG. 4 is a variant of FIG. 1. References (1) to (5) and (7) to (11) of FIG. 4 are identical to those of FIG. 1.

The installation in FIG. 4 comprises a first purification device (130) connected to the inlet of the first separating device (5) via pipeline (60) and able to isolate a secondary mercaptan in a first line (160), a linear mercaptan in a second line (150) and sulphides in a third line (140).

The installation in FIG. 4 also comprises a line (170) conveying the sulphides and other by-products, connecting the outlet of the first purification device (130) to the inlet of the finishing reactor (8).

The installation in FIG. 4 finally comprises a second purificationdevice (18) connected to the outlet of the second separating device (10) via pipeline (120) and able to isolate a mercaptan in a first line (19) and sulphides in a second line (20).

More particularly, the invention relates to an installation for carrying out the process as defined above, said installation comprising:

an addition reactor (1), supplied with hydrogen sulphide and with olefin via pipelines (2, 3), a pipeline (4), connected to the outlet of the addition reactor (1), supplies a first separating device (5) with a stream of crude reaction mixture, a pipeline (7), connected to the outlet of the first separating device (5), supplies a finishing reactor (8) with the light fraction comprising the excess hydrogen sulphide and the olefins, a pipeline (9), connected to the outlet of finishing reactor (8), supplies a second separating device (10) with all of the reaction mixture from the finishing reactor (8), a pipeline (11) located at the outlet of the second separating device (10) recycles the fraction rich in hydrogen sulphide to the addition reactor (1) and pipelines (12, 6, 120, 60) coming from the first and second separating devices (5, 10) recover the heavy fraction comprising at least one mercaptan and optionally one or more thioethers and the fraction rich in addition products.

According to a preferred embodiment, pipelines (12, 6) coming from the first and second separating devices (5, 10) recover the heavy fraction comprising at least one mercaptan and optionally one or more thioethers and the fraction rich in addition products, combining them in a single pipeline.

The following examples are given by way of illustration of the present invention.

EXAMPLES OF LABORATORY IMPLEMENTATION OF THE CATALYTIC ADDITION OF HYDROGEN SULPHIDE TO A TERMINAL OLEFIN

Example 1

Process According to the Invention

The step of addition of hydrogen sulphide to a butene-1 is carried out in the following conditions:
1—First fixed-bed catalytic reactor charged with 200 cm$^3$ of catalyst (19% $Cr_2O_3$/Alumina):
Butene-1: 75 g/h
$H_2S$: 92 NL/h, corresponding to a molar ratio $H_2S$/butene=2
Average temperature of the catalyst bed=245° C.

P=1.4 MPa
LHSV=60 h$^{-1}$
The results obtained for this addition step are as follows:
Conversion: 83%
Selectivities: 81/14/5 (SBM/NBM/thioethers)
The unconverted butenes then have the following molar composition:
10% butene-1/45% butene-2 cis/45% butene-2 trans
The fraction of unconverted butenes goes into the finishing reactor according to the following conditions:
2—Fixed-bed finishing reactor charged with 100 cm$^3$ of sulphonic resin A36 dry (DOW)
Butenes: 7.3 NL/h
H$_2$S: 120 NL/h
LHSV=120 h$^{-1}$
No solvent.
The results obtained for this finishing step are as follows:
Conversion: 97.5%
Selectivities: 87% SBM, 13% thioethers
These two steps thus lead to a conversion of 99.5% of butene-1 and the following selectivity:
SBM: 81.6%
NBM: 11.6%
Sulphides: 6.2%
with a supply of butenes of: 99.5% butene-1/0.5% butenes-2.

Example 2

Comparative Process

The first step of the process is identical to that of example 1.
1—Fixed-bed catalytic reactor charged with 200 cm$^3$ of catalyst (19% Cr$_2$O$_3$/Alumina):
Butene-1: 75 g/h
H$_2$S: 92 NL/h corresponding to a molar ratio H$_2$S/butene=2
Average temperature of the catalyst bed=245° C.
P=1.4 MPa
LHSV=60 h$^{-1}$
Performance:
Conversion: 83%
Selectivities: 81/14/5 (SBM/NBM/thioethers)
The unconverted butenes then have the following molar composition:
10% butene-1/45% butene-2 cis/45% butene-2 trans
The fraction of unconverted butenes is recycled to the catalytic reactor according to the following conditions:
Supply of butenes: 75 g/h with 20% butenes-2 in butene-1
H$_2$S: 92 NL/h corresponding to a molar ratio H$_2$S/butene=2
Average temperature of the catalyst bed=245° C.
P=1.4 MPa
LHSV=80 h$^{-1}$
These steps of addition and recycling lead to a conversion of 60% and a selectivity of 82/12/6 (SBM/NBM/thioethers).
The butenes-2, not reacting, lead to a drop in productivity and accumulate in the recycling, finally making the process inoperative.

The invention claimed is:
1. A process for synthesis of a mercaptan starting from a terminal olefin and hydrogen sulphide comprising at least the following successive steps:
A—catalytically adding hydrogen sulphide to a terminal olefin catalysed by an acid catalyst, then
B—separating the products of the addition reaction into a light fraction comprising the excess hydrogen sulphide and the olefins, and
a heavy fraction comprising at least one mercaptan and optionally one or more thioethers,
C—in a finishing step, passing the light fraction obtained from step B over an acid catalyst, then
D—separating the products from the finishing step into a fraction rich in hydrogen sulphide and
a fraction rich in addition products and then
E—recycling the fraction rich in hydrogen sulphide to step A.
2. A process according to claim 1, wherein the mercaptan synthesized is a secondary mercaptan.
3. A process according to claim 1, wherein the catalyst used in the addition step is a catalyst comprising Lewis acid sites.
4. A process according to claim 1, wherein the addition reaction in step A and/or step C is or are heterogeneous catalyses using a solid acid catalyst.
5. A process according to claim 3, wherein the catalyst comprising Lewis acid sites is selected from the group consisting of oxides of molybdenum, oxides of cobalt, oxides of chromium, cobalt molybdate, phosphotungstic acids deposited on supports selected from activated carbon, alumina, zirconia, silica, thorium oxide, pumice stone or silica-alumina compositions.
6. A process according to claim 1, wherein the terminal olefin is of the following general formula (1):

$$R_1R_2C=CH_2 \qquad (1),$$

in which R$_1$ denotes a hydrogen atom, and
R$_2$ represents an alkyl radical with from 1 to 20 carbon atoms, linear, branched or cyclic.
7. A process according to claim 6, wherein the terminal olefin is 1-butene.
8. A process according to claim 1, wherein the catalyst used for the finishing step is an acid catalyst that has strong acid sites.
9. A process according to claim 1, wherein the process comprises the following additional step:
F—combining and then purifying the heavy fraction obtained from ,separation step B and the fraction rich in addition products obtained from separation step D, to provide one or more light fractions comprising one or more mercaptans and
a heavy fraction comprising the sulphides.
10. A process according to claim 9, wherein the process comprises the following additional step:
G—recycling the heavy fraction from the purification step F to the finishing step C.
11. An installation for carrying out the process as defined in claim 1 comprising:
an addition reactor, supplied with hydrogen sulphide and with olefin via a first pipeline and a second pipeline,
a third pipeline, connected to an outlet of the addition reactor, which supplies a first separating device with a stream of crude reaction mixture,
a fourth pipeline, connected to an outlet of the first separating device, which supplies a finishing reactor with the light fraction comprising the excess hydrogen sulphide and the olefins,
a fifth pipeline, connected to an outlet of the finishing reactor, which supplies a second separating device with all of the reaction mixture from the finishing reactor,
a sixth pipeline located at an outlet of the second separating device which recycles the fraction rich in hydrogen sulphide to the addition reactor, additional pipelines coming from the first and second separating devices which recover the heavy fraction comprising at least one mercaptan and optionally one or more thioethers and the fraction rich in addition products, and
a single pipeline combining the heavy fraction comprising at least one mercaptan and optionally one or more thioethers and the fraction rich in addition products.

12. An installation according to claim 11, wherein the installation comprises a purification device, connected to the single pipeline, the purification device being able to isolate a secondary mercaptan in a first line, a linear mercaptan in a second line and to discharge a heavy fraction comprising the sulphides and other by-products in a third line.

13. An installation according to claim 12, wherein the installation comprises a fourth line, connected to the outlet of the purification device, conveying the sulphides and other by-products, the fourth line supplying the finishing reactor.

14. A process according to claim 3, wherein the catalyst comprising Lewis acid sites is chromium oxide supported on alumina.

15. A process according to claim 6, wherein $R_2$ represents an alkyl radical with from 2 to 12 carbon atoms, linear, branched or cyclic.

16. A process according to claim 1, wherein the catalyst used for the finishing step is selected from the group consisting of cation exchange resins and zeolites, whether exchanged or not.

* * * * *